United States Patent
Hines et al.

(10) Patent No.: US 7,976,505 B2
(45) Date of Patent: Jul. 12, 2011

(54) DISPOSABLE INFUSION DEVICE NEGATIVE PRESSURE FILLING APPARATUS AND METHOD

(75) Inventors: Craig Hines, San Francisco, CA (US); Cory Williamson, Austin, TX (US)

(73) Assignee: Calibra Medical, Inc., Redwood City, CA (US)

( * ) Notice: Subject to any disclaimer, the term of this patent is extended or adjusted under 35 U.S.C. 154(b) by 310 days.

(21) Appl. No.: 12/004,479

(22) Filed: Dec. 19, 2007

(65) Prior Publication Data

US 2009/0163866 A1 Jun. 25, 2009

(51) Int. Cl.
*A61M 5/32* (2006.01)
(52) U.S. Cl. .............. 604/180; 604/890.1; 604/131; 141/323
(58) Field of Classification Search .............. 604/407, 604/257, 180, 131; 141/330
See application file for complete search history.

(56) References Cited

U.S. PATENT DOCUMENTS

| | | | |
|---|---|---|---|
| 4,360,019 A | 11/1982 | Portner et al. | |
| 4,604,090 A * | 8/1986 | Reinicke | 604/118 |
| 4,684,365 A * | 8/1987 | Reinicke | 604/126 |
| 5,921,962 A * | 7/1999 | Kriesel et al. | 604/132 |
| 6,537,249 B2 | 3/2003 | Kriesell et al. | |
| 6,685,673 B2 * | 2/2004 | Minezaki et al. | 604/143 |
| 2007/0282269 A1 * | 12/2007 | Carter et al. | 604/164.01 |

OTHER PUBLICATIONS

International Search Report for International Patent Application No. PCT/US2008/087219, dated Jun. 24, 2009.

* cited by examiner

*Primary Examiner* — Nicholas D Lucchesi
*Assistant Examiner* — Leah Stohr
(74) *Attorney, Agent, or Firm* — Richard O. Gray, Jr.; Graybeal Jackson LLP

(57) ABSTRACT

An infusion system comprises a disposable wearable infusion device having a body arranged to be adhered to a patient's skin and a reservoir for holding a liquid medicament to be infused into the patient and a filler assembly arranged to be detachably received by the infusion device. The filler assembly is configured to receive a source of liquid medicament and provides a negative pressure to pull liquid medicament from the source of medicament to the infusion device reservoir.

18 Claims, 3 Drawing Sheets

DISPOSABLE INFUSION DEVICE NEGATIVE PRESSURE FILLING APPARATUS AND METHOD

BACKGROUND OF THE INVENTION

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have been shown to improve control of blood glucose levels. However, they suffer the drawbacks of size, cost, and complexity. For example, these pumps are electronically controlled and must be programmed to supply the desired amounts of basal and bolus insulin. This prevents many patients from adopting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin their device must carry to provide treatment over a fixed time period of, for example, three days. This is one environment where one size does not fit all. Another problem is with cannula deployment to support insulin delivery. Cannula deployment to support delivery of the insulin beneath the patient's skin must be made easy and convenient. This is not as easy as it seems because cannula deployment, as generally and currently performed in the art, requires insertion of a cannula carrying needle into the patient and then retraction of only the needle to leave the cannula in place beneath the patient's skin.

Still further, medical devices, such as IV pumps, insulin pumps and the like, designed to deliver liquid medicaments to patients by means of intravascular, intramuscular or interstitial injection are subject to problems due to difficulties in filling with the medicament prior to use. Specifically, the process of transferring a liquid medicament from a storage vial to the drug delivery device can be both difficult and error prone. The difficulty can be caused by the need to maintain sterility of the contacting surfaces, and the logistics of using an intermediate transfer device such as a syringe. Errors can be caused by miss-measurement of fluids and by the inadvertent introduction of air into the drug delivery device. While the difficulties can be inconvenient, the errors can result in more serious problems such miss-dosing. The consequences of incorrect treatment due to miss-dosing can vary from minor to serious. In the case of insulin delivery, incorrect dosing can lead to acute hypoglycemia or chronic hyperglycemia.

One currently proposed method of preparing a disposable insulin delivery device for use includes transferring insulin from a liquid medicament vial to the insulin delivery device. As proposed, this may be accomplished with a syringe and mounted needle by first drawing an amount of air into the syringe equal to the amount of insulin that will be withdrawn from the vial. Next, the vial septum is pierced with the needle and air is injected from the syringe into the vial, thus pressurizing the vial. The desired amount of insulin is then withdrawn from the vial into the syringe and thereafter, the needle is withdrawn from the vial. Next, the syringe is held in a vertical orientation to allow entrapped air to rise to the top. The syringe plunger is then gently advanced until the air has been ejected and a small amount of fluid is expressed from the syringe. The septum on the medicament delivery device is then pierced with the syringe to access the device reservoir and the insulin is injected into the reservoir. Lastly, the reservoir is inspected for air bubbles and those larger than 1 mm in diameter are removed by reinserting the syringe needle and aspirating the bubble.

This foregoing procedure is subject to error during the syringe filling and degassing steps, and during the reservoir filling step. Error during either step can result in excess air injected into the medicament delivery device. Excess air in the reservoir of the medicament delivery device can adversely affect the amount of insulin delivered to the patient during use, thereby compromising treatment.

Hence, there is a need for an improved filling device and method that will reduce the complications and potential errors associated with transferring a medicament from a storage vial to a drug delivery device. As will be seen subsequently, the present invention addresses these and other issues.

SUMMARY OF THE INVENTION

In one embodiment, the invention provides an infusion system. The infusion system comprises a disposable wearable infusion device having a body arranged to be adhered to a patient's skin, a reservoir for holding a liquid medicament to be infused into the patient and a filler assembly arranged to be detachably received by the infusion device. The filler assembly is configured to receive a source of liquid medicament and provides a negative pressure to pull liquid medicament from the source of medicament to the infusion device reservoir.

The source of liquid medicament may be a vial of the liquid medicament. The filler assembly may be arranged to pull a set volume of the liquid medicament from the source of liquid medicament to the infusion device reservoir. The filler may include a vacuum pump that pulls the liquid medicament from the source of liquid medicament to the infusion device reservoir.

The infusion device reservoir may be expandable and the filler may include an expander that provides the negative pressure by expanding the volume of the infusion device reservoir to pull the liquid medicament from the source of liquid medicament to the infusion device reservoir. The expander may be within the infusion device reservoir. Alternatively, the expander may be external to the reservoir.

The expander may include a vacuum pump. The infusion device reservoir may include a flexible diaphragm and the expander may be arranged to act upon the flexible diaphragm to expand the infusion device reservoir.

In another embodiment, a method comprises the steps of providing a disposable infusion device adapted to adhere to a patient's skin and having a reservoir for holding a liquid medicament to be infused into the patient and coupling a medicament filler, including a source of liquid medicament, to the infusion device reservoir. The method further comprises the step of filling the infusion device reservoir with the liquid medicament by pulling the medicament from the source of liquid medicament into the infusion device reservoir.

The coupling step may comprise detachably joining the medicament filler to the infusion device. The coupling step may further comprise providing the medicament filler with a vial of the liquid medicament.

The infusion device reservoir may be flexible and the pulling step may include expanding the infusion device reservoir. The expanding step may be performed from within the infusion device reservoir. Alternatively, the expanding step may be performed from outside the infusion device reservoir. The expanding step may include pulling a vacuum against the infusion device reservoir.

In a further embodiment, the invention provides a filler system for filling a reservoir of a disposable wearable infusion device with a liquid medicament. The system comprises an outlet arranged to be detachably received by the infusion device, a source of liquid medicament, and a siphon arranged to provide a negative pressure to pull liquid medicament from the source of medicament to transfer a volume of the liquid medicament to the infusion device reservoir.

The source of liquid medicament may be a vial of the liquid medicament. The siphon may include a vacuum pump that pulls the liquid medicament from the source of liquid medicament to the infusion device reservoir.

The infusion device reservoir may be expandable and the siphon may include an expander that expands the volume of the infusion device reservoir to pull the liquid medicament from the source of liquid medicament to the infusion device reservoir. The expander may be within the infusion device reservoir. Alternatively, the expander may be external to the reservoir. The expander may include a vacuum pump.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
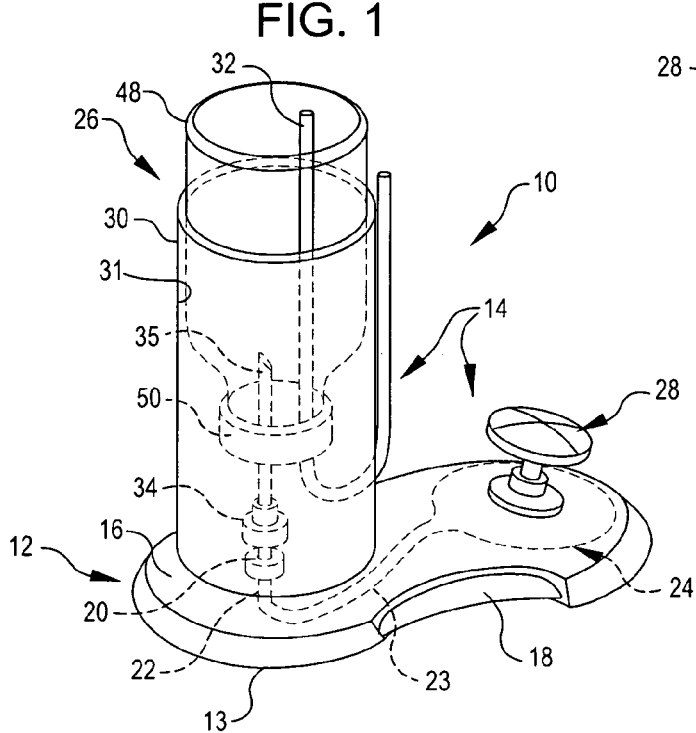
FIG. 1 is a perspective view of an infusion system including a medicament filling apparatus according to a first embodiment of the present invention.

Referring now to FIG. 1, it is a perspective view of an infusion system 10 according to a first embodiment of the present invention. The system 10 generally comprises a wearable disposable infusion device 12 and a liquid medicament filling device 14.

The infusion device 12 generally includes a housing 16, at least one actuator button 18, a fill port 20, and a reservoir 24. The housing has a bottom surface 13 that may be adhered to a patient's skin in a manner well known within the art. The device 12 also includes a conduit 23 that provides fluid communication between the port 20 and reservoir 24. The device is preferably arranged to receive a cannula (not shown) after it is filled with liquid medicament, such as insulin, to be administered to the wearer of the device 12. The actuator button 18 may be one of two actuator buttons which require concurrent actuation to cause the liquid medicament to be delivered. This arrangement helps to prevent accidental dosing. The fill port 20 may include a septum (not shown) that may be pierced by a needle 22 carried by the filling device 14 during the filling of device reservoir 24. This serves to promote sterility during the filling process. To these and other ends, the infusion device may take a form as shown, and described, for example, in U.S. application Ser. No. 11/604,166, filed Nov. 22, 2006 for DISPOSABLE INFUSION DEVICE FILLING APPARATUS AND METHOD, which application is owned by the assignee of the present invention and incorporated herein by reference in its entirety.

The filling device 14 generally includes a liquid medicament source 26 and a vacuum/fill pump 28. The source 26 includes a generally cylindrical housing 30, a vent tube 32, a pressure activated one way valve 34 and a second needle 35. The vacuum pump 28 includes a release valve 36, a pump actuator 38, a sterile needle 40, a seal 42, and a measured volume indicator 44. The release valve 36 also serves as a back up seal to needle 40.

The housing 30 has a cavity 31 dimensioned to receive a vial 48 containing the insulin or other liquid medicament. The medicament source 26 is detachably received on the body 16 of the infusion device 12 for the filling of the reservoir 24. More particularly, it may be noted that the port 20 is adapted to receive the needle 22 of the medicament source 26 as the source 26 is detachably received by the device 12. When the vial 48 is received within the housing 30, the end cap 50 of the vial 48 is pierced first by the vent tube 32 and then by the needle 35. The length of the vent tube 32 is selected so that when the vial 48 is fully received within the housing 30, the end of the vent tube 32 extends above the liquid medicament. The vent tube 32 thus permits the liquid medicament to flow freely from the vial 48, through the pressure activated one-way valve 34, and into the port 20.

Figure 2:
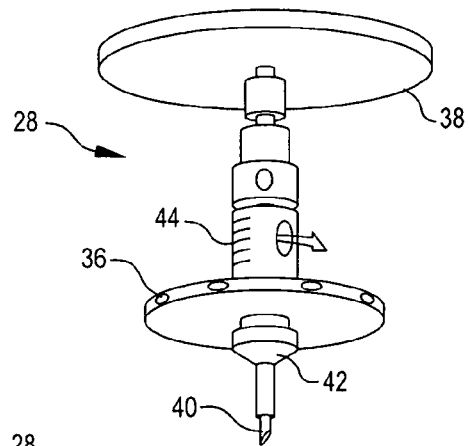
FIG. 2 is a perspective view illustrating details of the filling apparatus of FIG. 1.

The vacuum/fill pump 28 is shown in greater detail in FIG. 2. The vacuum/fill pump 28 may be mounted on the device 12 with the sterile needle 40 piercing another septum (not shown) so that the needle 40 extends to within the reservoir 24. The seal 42 provides an effective seal so that air flows into and out of the reservoir is controlled by the pump 28. To that end, the pump 28 may selectively be a vacuum pump or a fill pump. The vacuum or fill functionality of pump 28 may be selected by rotating the actuator 38.

When both the source 26 and pump 28 are received on the device 12 as described above, the reservoir 24 of the device 12 is ready to be filled. First, the pump is used to pump air from port 45 into the reservoir 24. When the reservoir 26 is full of air, the actuator 38 is rotated to convert the pump 28 into a vacuum pump. Depressing the actuator 38 now causes air to be sucked out of the device reservoir 24 and out port 45. This results in a negative pressure within the reservoir 24. When the negative pressure exceeds the set point of the pressure activated one way valve 34, liquid medicament within the vial 48 will flow through conduit 23 and into the reservoir 24. The filling assembly 14 is arranged to transfer a set volume of liquid medicament from the vial 48 into the reservoir 24. This may be accomplished by counting the number of depressions of the actuator 38 or by noting the volume on the measured volume indicator 44.

When the desired quantity of liquid medicament has been transferred to the device reservoir 24, the filling assembly 14 is removed from the infusion device 12 with the needle 22 being removed from the port 20 and the needle 40 being removed from its corresponding port (not shown). The filling assembly 14 may now be placed into sterile storage with the vial 48 remaining in the housing 30. Such storage supports multiple use of the filling device.

Figure 3:
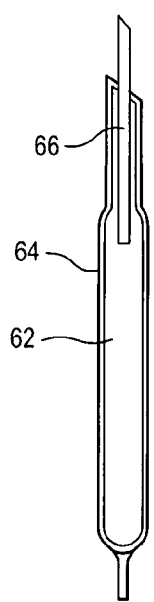
FIG. 3 is a side view of an infusion device reservoir to be filled with a liquid medicament according to a second embodiment of the present invention.

FIGS. 3-6 schematically illustrate the general filling and use of an infusion device reservoir to be filled with a liquid medicament according to a second embodiment of the present invention. Referring initially to FIG. 3, it shows the reservoir 62 to be filled confined within an enclosure 64. The reservoir is formed of flexible or expandable material. The reservoir includes a needle 66, also within the enclosure 64, that communicates with the interior of the reservoir 62.

Figure 4:
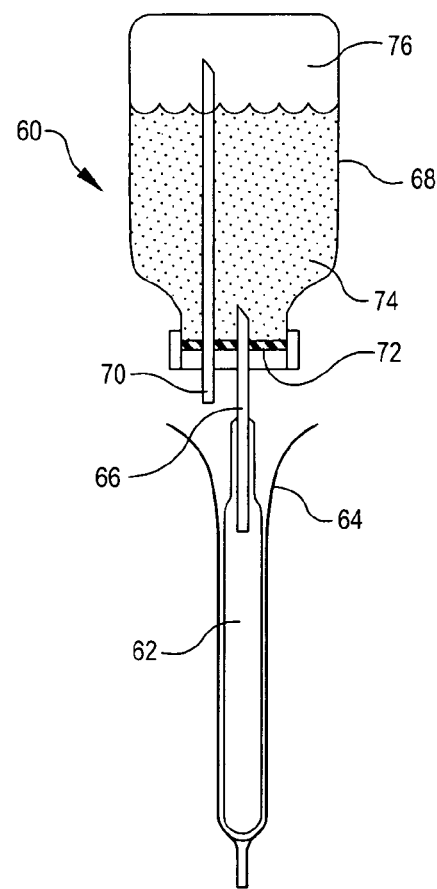
FIG. 4 is a side view of the infusion device reservoir of FIG. 3 joined with the medicament source of a medicament filling apparatus according to the second embodiment of the present invention.

Referring now FIG. 4, here it may be seen that the needle 66 forms part of a filling system 60 for filling the reservoir 62. The filling system 60 also includes a vial 68, and a vent tube 70. The vial 68 includes a septum 72 through which the needle 66 and vent tube 70 extend. The vent tube 70 extends to above the fill line of the liquid medicament 74 into a head space 76.

Figure 5:
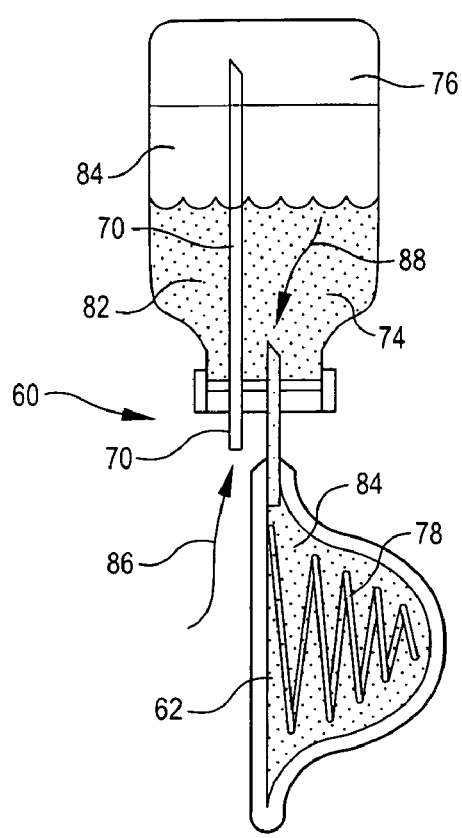
FIG. 5 is side view illustrating the filling of the infusion device reservoir of FIG. 3.

FIG. 5 shows the reservoir 62 being filled. The needle 66 has been inserted through the septum 72. The filling system 60 further includes a spring 78 that is compressed when the reservoir 62 is confined within the enclosure 64. However, when the enclosure 64 is unsealed as shown in FIG. 4 permitting the needle 66 to penetrate the septum 72 and the enclosure 64 is removed from the reservoir, the reservoir 62 will expand, causing liquid medicament to be drawn into it. More specifically, when the reservoir 62 expands under the influence of the internal expander formed by the spring 78, a negative pressure is created within the reservoir 62 causing the liquid medicament to flow into needle in the direction indicated by reference numeral 88 and into the reservoir 62. The volume of liquid medicament displaced 82 is replaced by air drawn in through the vent tube in the direction indicated by reference numeral 86. When the reservoir 62 is fully expanded, the reservoir will be filled with liquid medicament 84.

Figure 6:
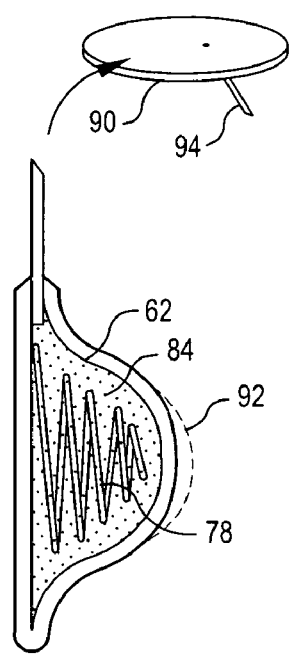
FIG. 6 is a side view of the infusion device reservoir of FIG. 3 as liquid medicament is being metered out therefrom.

FIG. 6 schematically illustrates the reservoir 62 in use after being filled with liquid medicament 84. Here, the reservoir 62 is providing liquid medicament to a cannula 94 of an infusion device 90. This may be accomplished by physically compressing the reservoir 62 and spring 78 as illustrated by the dashed line 92. Alternatively, the reservoir may be coupled to a pump (not shown) within the infusion device 90 in a manner as shown hereinafter in FIGS. 7 and 8 for drawing the liquid medicament from the reservoir 62 against the expansion force of the spring 7As may be appreciated by those skilled in the arts instead of the spring being within the reservoir as shown in FIGS. 5 and 6, of the reservoir. This would then continue the spring to be external to the reservoir.

Figure 7:
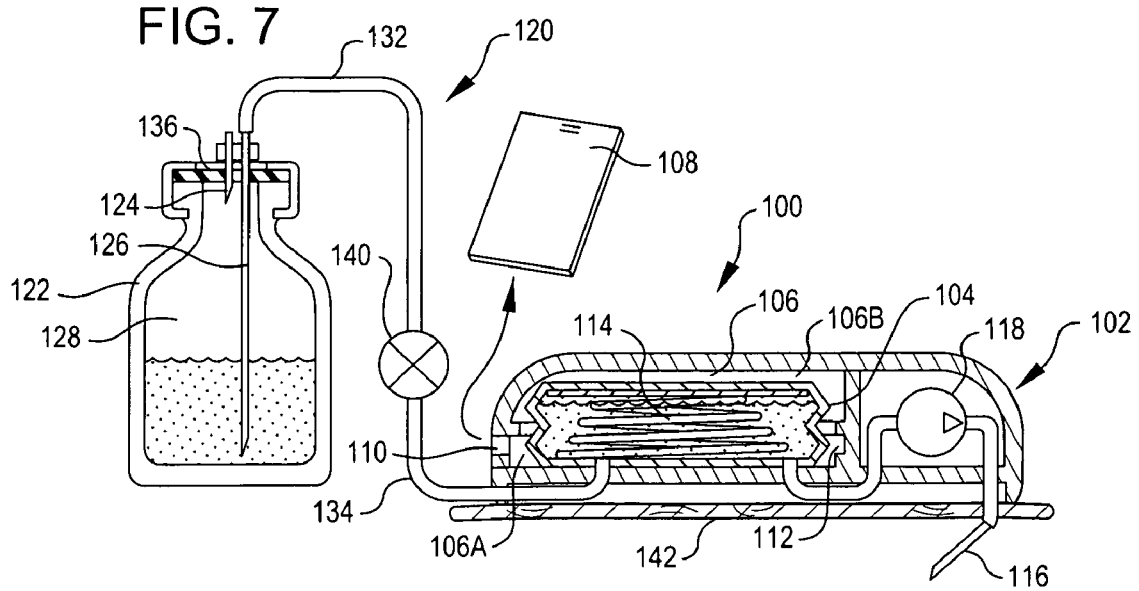
FIG. 7 is a sectional side view illustrating an infusion system embodying the invention including an infusion device having a reservoir being filled with a liquid medicament.

FIG. 7 is a sectional side view illustrating an infusion system 100 including an infusion device 102 having a reservoir 104 being filled with a liquid medicament. The reservoir 104 is being filled by a filling system 120 according to another embodiment the invention. The reservoir 104 is disposed and confined within a chamber 106 of the device 102 The chamber 106 comprises a lower chamber 106A and an upper chamber 106B. The reservoir 104 again, is formed of a flexible or expandable material. The volume of the chamber 106 is initially determined by a relatively rigid removable panel 108 originally bridging the reservoir 106 and confined by slot 110 and recess 112 to define the lower chamber 106A. When the panel 108 is removed through the slot 110, the reservoir 104 as described above expands into the upper chamber 106B, in a manner as schematically shown in FIGS. 3-6, under the influence of spring 114. The reservoir 104 will now occupy all of chamber 106.

As in the embodiment of FIGS. 3-6, the spring 114 forms part of the filling system 120 for filling the reservoir 104. The filling system 120 also includes a vial 122 and a vent tube 124. The vial 122 includes a septum 136 through which a filling needle 126 and the vent tube 124 extend. The vent tube 120 vents the interior 128 of the vial 122 to atmospheric pressure. The reservoir 104 is coupled to the filling tube 126 by conduits 132 and 134 and a pressure controlled valve 140.

When the reservoir 104 is to be filled with liquid medicament, the device 102 is coupled to the filling tube 126 by inserting the conduit 134 into the reservoir 104. Then, the panel 108 is removed and the reservoir 104 expands under the influence of the spring 114. This creates a negative pressure within the reservoir that is translated to the conduit 134 causing the valve 140 to open. Liquid medicament will now flow into the needle 126, through conduit 132, through valve 140 and through conduit 134 into the reservoir 104. The volume of liquid medicament displaced within the vial 122 is replaced by air drawn in through the vent tube 124. When the reservoir 104 is fully expanded, a set volume of liquid medicament has been transferred to the device reservoir and the filling procedure is completed.

The device 102 filled with the liquid medicament is now ready for use. To that end, the device may be detached from the filling assembly 120 and adhered to a patient's skin 142 in a manner as is know in the art. In use, the reservoir 104 may provide liquid medicament to a cannula 116 that extends beneath the skin 142 of the patient under the influence of a pump 118 of the infusion device 102. The pump 118 within the infusion device 102, when actuated, draws the liquid medicament from the reservoir 104 against the expansion force of the spring 114 and provides the same to the cannula 116.

Figure 8:
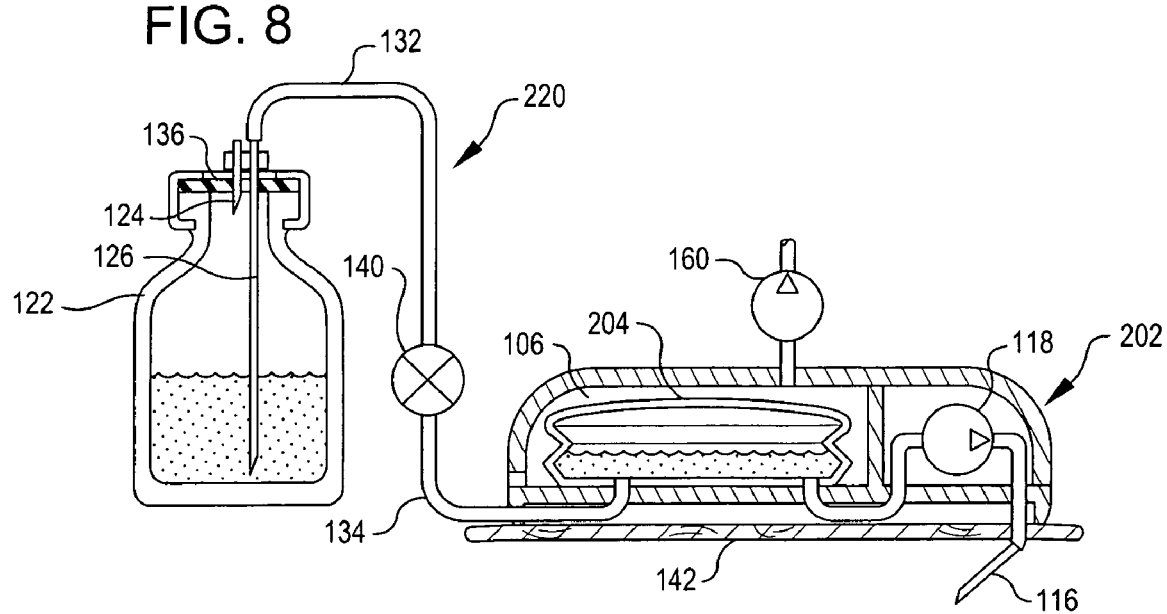
FIG. 8 is a sectional side view illustrating a further infusion system embodying the invention including an infusion device having a reservoir being filled with a liquid medicament.

FIG. 8 is a sectional side view illustrating a further infusion system according to another embodiment of the invention, similar to the infusion system of FIG. 7. Structural elements of FIG. 8 corresponding to those of FIG. 7 are provided with corresponding reference numerals. The infusion system of FIG. 8 generally includes an infusion device 202 and a filling system 220.

The filling system 220 includes the vial 122 and the vent tube 124. The vial 122 includes the septum 136 through which the filling needle 126 and the vent tube 124 again extend. The vent tube 120, as before, vents the interior 128 of the vial 122 to atmospheric pressure. The filling system also includes the conduit 132, the pressure controlled valve 140 and the conduit 134.

The reservoir 104 is coupled to the filling tube 126 by conduits 132 and 134 and a pressure controlled valve 140.

The infusion device 202 includes a reservoir 204 to be filled with a liquid medicament. The reservoir 204 is in the form of an expandable diaphragm and is coupled to the filling tube 126 by the conduits 132 and 134 and the pressure controlled valve 140. The device also includes the cannula 116 and the pump 118.

The chamber 106 of the device 202, according to this embodiment has a fixed volume. It is coupled to a vacuum pump 160 of the filling system 220. Whereas the reservoir 104 of the device 102 of FIG. 7 is expanded under the influence of the internal spring 114, the reservoir 204 of the device 202 is expanded under the influence of a vacuum applied to the chamber 106 and the reservoir 204 by the external vacuum pump 160.

When the reservoir 204 is to be filled with liquid medicament, the device 202 is coupled to the filling tube 126 by inserting the conduit 134 into the reservoir 204. Then, the vacuum pump 160 is activated and the reservoir 204 expands under the influence of the vacuum pulled in chamber 106. Thus, the reservoir is expanded by means external to the reservoir. This creates a negative pressure within the reservoir 204 that is translated to the conduit 134 causing the valve 140 to open. Liquid medicament will now flow into the needle 126, through conduit 132, through valve 140 and through conduit 134 into the reservoir 204. As in the previous embodiment, the volume of liquid medicament displaced from the vial 122 is replaced by air drawn in through the vent tube 124. When the reservoir 204 is fully expanded, the filling procedure is completed. The device is now ready for use to deliver liquid medicament to the cannula beneath the patient's skin 142 in the manner as previously described with reference to FIG. 7.

While particular embodiments of the present invention have been shown and described, modifications may be made, and it is therefore intended in the appended claims to cover all such changes and modifications which fall within the true spirit and scope of the invention as defined by those claims.

What is claimed is:

1. An infusion system comprising:
   a disposable wearable infusion device having a body arranged to be adhered to a patient's skin and a reservoir for holding a liquid medicament to be infused into the patient; and
   a filler assembly arranged to be detachably received by the infusion device, the filler configured to receive a source of liquid medicament and providing a negative pressure to pull liquid medicament from the source of medicament to the infusion device reservoir.

2. The system of claim 1, wherein the source of liquid medicament is a vial of the liquid medicament.

3. The system of claim 1, wherein the filler assembly is arranged to pull a set volume of the liquid medicament from the source of liquid medicament to the infusion device reservoir.

4. The system of claim 1, wherein the infusion device reservoir is expandable and wherein the filler includes an expander that provides the negative pressure and expands the volume of the infusion device reservoir to pull the liquid medicament from the source of liquid medicament to the infusion device reservoir.

5. The system of claim 4, wherein the expander is external to the reservoir.

6. The system of claim 5, wherein the expander includes a vacuum pump.

7. The system of claim 6, wherein the infusion device reservoir includes a flexible diaphragm and wherein the expander acts upon the flexible diaphragm to expand the infusion device reservoir.

8. A method comprising: providing a disposable infusion device adapted to adhere to a patient's skin and having a reservoir for holding a liquid medicament to be infused into the patient; providing a medicament filler including a source of liquid medicament and arranged to pull liquid medicament from the source of medicament to the infusion device reservoir; coupling the medicament filler to the infusion device reservoir; and filling the infusion device reservoir with the liquid medicament by pulling the medicament with the medicament filler from the source of liquid medicament into the infusion device reservoir.

9. The method of claim 8, wherein the coupling step comprises detachably joining the medicament filler to the infusion device.

10. The method of claim 8, wherein the coupling step further comprises providing the medicament filler with a vial of the liquid medicament.

11. The method of claim 8, wherein the infusion device reservoir is expandable and wherein the pulling step includes expanding the infusion device reservoir.

12. The method of claim 11, wherein the expanding step is performed from outside the infusion device reservoir.

13. The method of claim 12, wherein the expanding step includes pulling a vacuum against the infusion device reservoir.

14. A filler system for filling a reservoir of a disposable wearable infusion device with a liquid medicament, comprising:
    an outlet arranged to be detachably received by the infusion device;
    a source of liquid medicament; and
    a negative pressure generator arranged to provide a negative pressure to pull liquid medicament from the source of medicament to transfer a volume of the liquid medicament to the infusion device reservoir.

15. The system of claim 14, wherein the source of liquid medicament is a vial of the liquid medicament.

16. The system of claim 14, wherein the infusion device reservoir is expandable and wherein the negative pressure generator includes an expander that expands the volume of the infusion device reservoir to pull the liquid medicament from the source of liquid medicament to the infusion device reservoir.

17. The system of claim 16, wherein the expander is external to the reservoir.

18. The system of claim 17, wherein the expander includes a vacuum pump.

* * * * *